United States Patent [19]

Alers et al.

[11] 4,104,922

[45] Aug. 8, 1978

[54] ELECTROMAGNETIC TRANSDUCER

[75] Inventors: George A. Alers; Robert B. Thompson, both of Thousand Oaks, Calif.

[73] Assignee: Rockwell International Corporation, El Segundo, Calif.

[21] Appl. No.: 801,674

[22] Filed: May 31, 1977

[51] Int. Cl.² .......................................... G01N 29/04
[52] U.S. Cl. ....................................... 73/643; 73/623
[58] Field of Search ................. 73/67.5 R, 67.6, 67.7, 73/67.8 R, 67.8 S, 71.5 US, 643; 324/37, 164, 40

[56] References Cited

U.S. PATENT DOCUMENTS

| 2,519,367 | 8/1950 | Gunn et al. | 324/40 |
| 3,535,624 | 10/1970 | Wood | 324/37 |
| 3,850,028 | 11/1974 | Thompson et al. | 73/71.5 US |

OTHER PUBLICATIONS

J. H. Meier, Analog No-Contact Transducer, I.B.M. Tech. Disclosure Bulletin, vol. 17, No. 11, pp. 3250–3251, Apr. 1975.

G. M. Berkin, Magnetic Tachometer, I.B.M. Tech. Disclosure Bulletin, vol. 3, No. 3, Aug. 1960.

W. D. Wallace, Electromagnetic Generation of Ultrasound in Metals, International Journal of Nondestructive Testing, vol. 2, No. 4, 1971, pp. 309–334.

*Primary Examiner*—Richard C. Queisser
*Assistant Examiner*—John P. Beauchamp
*Attorney, Agent, or Firm*—L. Lee Humphries; Craig O. Malin

[57] ABSTRACT

An electromagnetic transducer is provided for ultrasonically inspecting conductive material as the material moves relative to the transducer. A coil is positioned in the field created by a magnet so that the conductors of the coil are transverse to the magnetic field. The coil is located predominantly near the leading side of the magnet where flux is concentrated as the magnet and material move toward each other.

8 Claims, 8 Drawing Figures

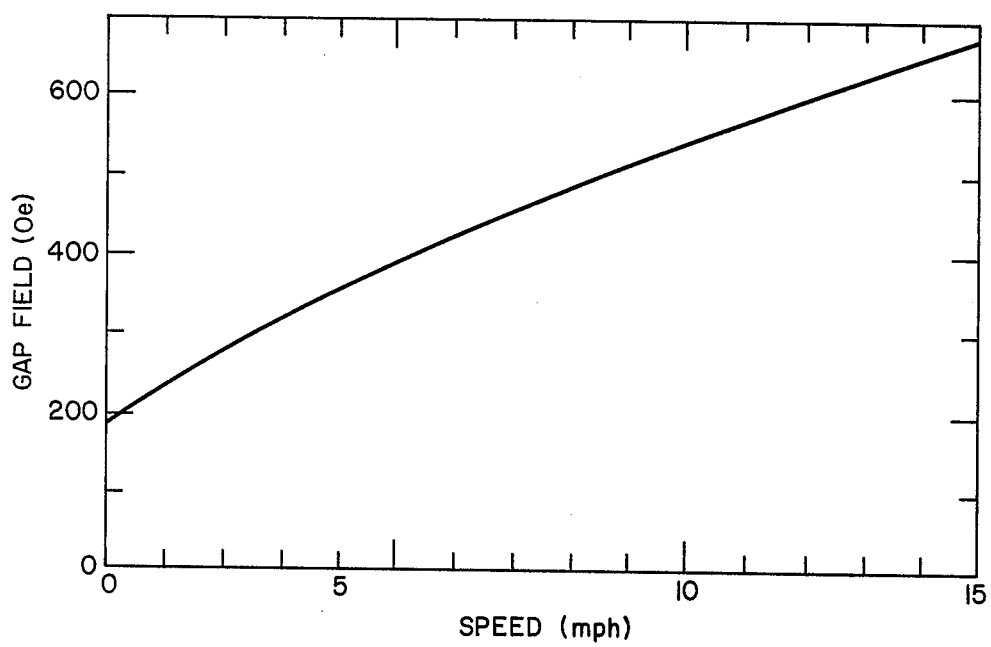
Fig. 4.
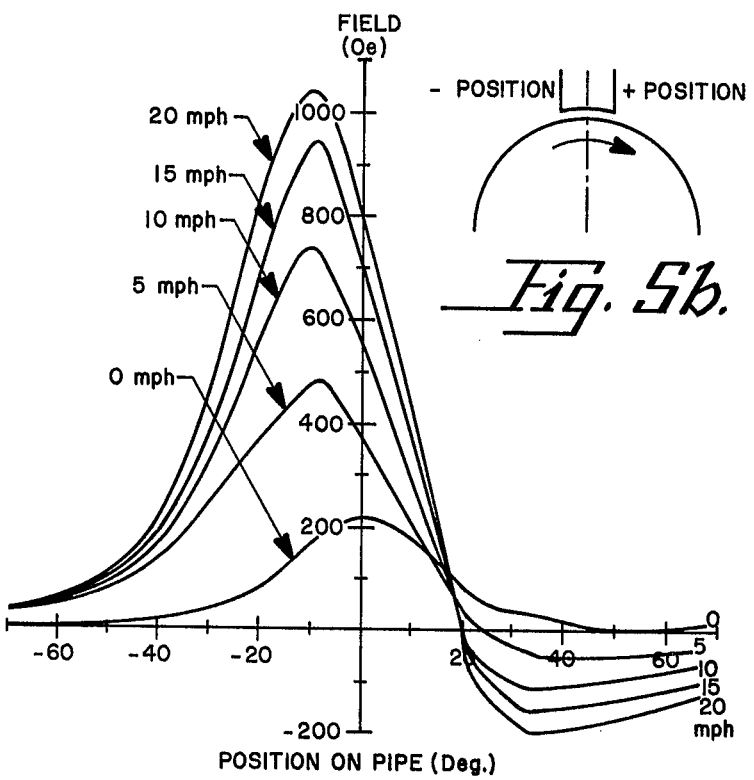
Fig. 5a.
Fig. 5b.

ELECTROMAGNETIC TRANSDUCER

BACKGROUND OF THE INVENTION

A. Field of the Invention

This invention relates to the field of inspection, and more particularly to the field of ultrasonic inspection of metals.

B. Description of the Prior Art

Ultrasonic waves can be generated in metals by a Lorentz force mechanism and, in magnetic materials, by both the Lorentz force mechanism and a magnetostriction mechanism. In both mechanisms, a coil is centered between the poles of a magnet adjacent to the surface of the metal and an RF current is fed through the coil. In the Lorentz force mechanism, the current in the coil induces eddy currents in the metal which react against an applied static magnetic field to produce the forces that launch the ultrasonic waves. In the magnetostriction mechanism, variations in the magnetic field, caused by the RF current cause changes in length in the magnetic material to create ultrasonic waves. Such types of electromagnetic transducers are used to generate ultrasonic Lamb waves, Rayleigh waves, and angle shear and longitudinal waves; and typical prior art transducers are exemplified by the meander coil and magnet disclosed in U.S. Pat. Nos. 3,850,028 to R. B. Thompson, G. A. Alers (the present inventors), and M. A. Tennison.

Electromagnetic transducers are ideal for use in moving inspection stations because they can generate elastic waves (generally referred to as ultrasonic waves) in the material being tested, without requiring physical contact with the material. They are noncontact transducers. However, their application has been limited by problems such as: (1) low signal generating efficiency, (2) high noise levels when used in motion with respect to ferromagnetic materials, and (3) the requirement of a large static magnetic field in the region of the RF coils.

The efficiency of the transducer depends upon the flux density of the applied static magnetic field. The field is generally furnished by a dc electromagnet which is bulky and consumes considerable power. This is a particularly severe problem for totally self-contained inspection stations which travel through pipelines, as described in U.S. Patent Application, No. 731,199 filed Oct. 12, 1976, to R. B. Thompson, G. A. Alers (the present inventors) and M. A. Tennison. The size of the electromagnets limits the minimum size of the pipe which can be inspected, and the power consumed by the batteries feeding the electromagnets limits the intensity and duration of the magnetic field which can be obtained. Thus, a method or structure which increases the intensity of the magnetic field without increasing the size or power consumed by the electromagnet is necessary to improve the efficiency of the transducer.

In a magnetic material, the low signal-to-noise ratio of electromagnetic transducers is caused by the Barkhausen effect noise generated when the transducer moves across the surface of the material. This noise is sufficient to obscure reflections from small defects in the material, particularly at test speeds of 1 to 2 mph. Until the present invention, this noise could only be suppressed by application of strong magnetic fields to a region large compared to the transducer.

SUMMARY OF THE INVENTION

It is an object of the invention to provide an efficient electromagnetic transducer.

It is an object of the invention to increase the efficiency of electromagnetic transducers without increasing the size or power consumed by the magnet which provides the magnetic field for the transducer.

It is an object of the invention to provide a method and device for increasing the maximum flux density of a magnetic field.

It is an object of the invention to provide an electromagnetic transducer having a high signal-to-noise ratio.

It is an object of the invention to provide an improved electromagnetic transducer for use in a self-contained, ultrasonic inspection station which travels through pipelines.

According to the invention, an electromagnetic transducer is provided for ultrasonically inspecting conductive material as the material moves relative to the transducer. A coil is positioned in the field created by a magnet so that the conductors of the coil are transverse to the magnetic field. The coil is located predominately near the leading side of the magnet where flux is concentrated as the magnet and material move toward each other.

These and other objects and features of the present invention will be apparent from the following detailed description, taken with reference to the accompanying drawings.

BRIEF DESCRIPTION OF THE DRAWINGS

FIG. 4 shows the relation between the density of the magnetic field in the gap and speed;

FIG. 5a is a plot of the distribution of the magnetic field at locations as shown in FIG. 5b for various speeds;

DESCRIPTION OF THE PREFERRED EMBODIMENT

Figure 1:
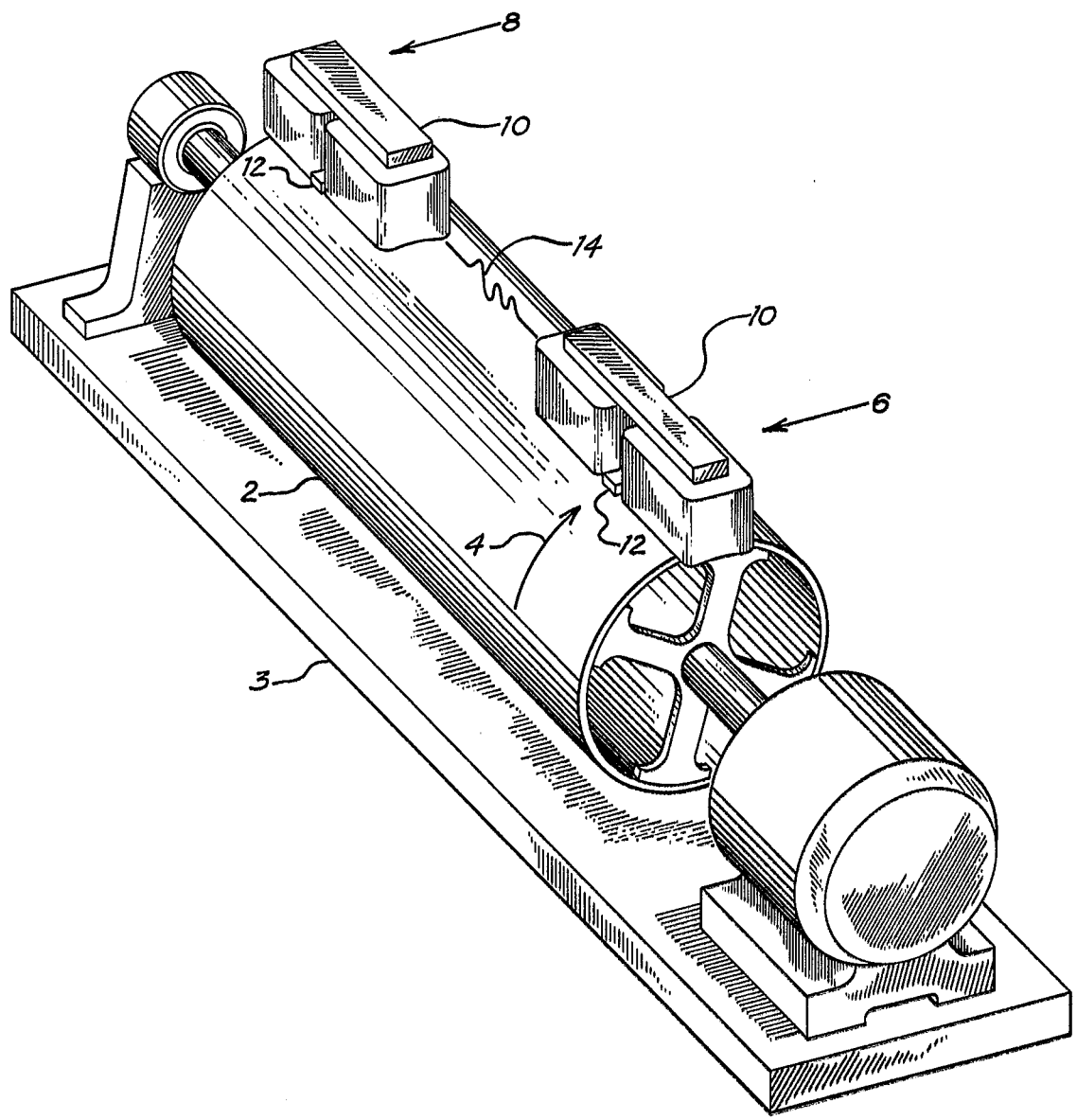
FIG. 1 is a schematic diagram of an embodiment of the invention that is particularly convenient to demonstrate the principles of the invention.

FIG. 1 is a schematic diagram of an embodiment of the invention which is convenient to demonstrate the principles upon which the present invention is based. Rather than run the transmitting and receiving transducers longitudinally through the inside of a long pipe as is done for actual in-place inspection of pipelines, a short section of pipe 2 is rotated in a lathe 3 as shown by arrow 4. The transmitting and receiving transducers 6, 8, respectively, are positioned concentrically to the outside surface of the pipe. Each transducer has an electromagnet 10 and a coil 12 positioned in the flux path between the poles of the magnet. When an RF signal is sent through coil 12 of transmitter 6, a Lamb wave 14 is generated. The Lamb wave is converted back to an electrical signal by receiver 8 in a reciprocal manner.

Figure 2:
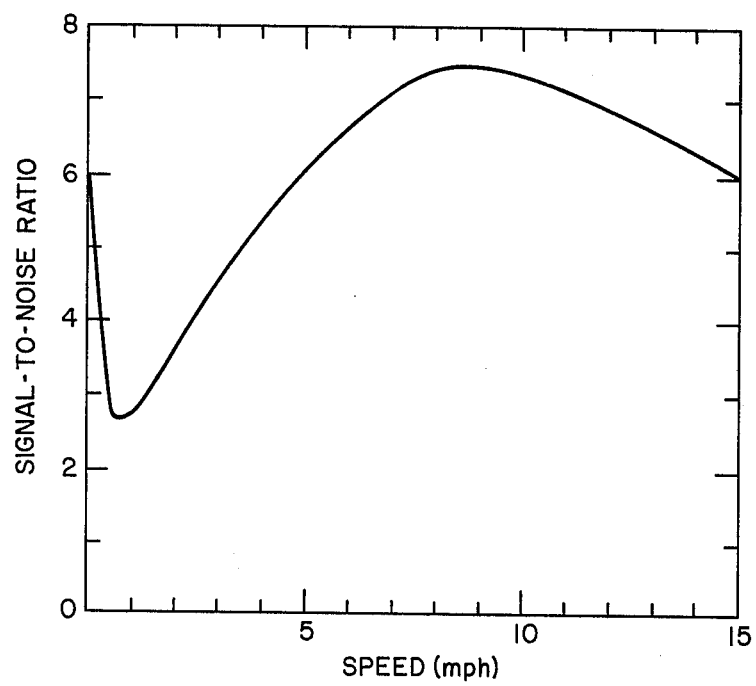
FIG. 2 shows the relation in pipeline-type steels between the signal-to-noise ratio and speed.

Utilizing the apparatus of FIG. 1, extensive studies were made of the speed related noise effect, and it was determined that, in ferromagnetic materials, the noise was produced by changes in magnetization that occur in the material as the transducer magnets move on to new, unmagnetized regions. The noise is a manifestation of the known Barkhausen effect in ferromagnetic materials. It was discovered by the work leading to the present invention that the noise signal increases with speed only at low speeds. It goes through a maximum at about 4 mph and then decreases with increasing speed in the range of speeds anticipated for practical inspection procedures. At the same time the amplitude of the received ultrasonic signal shows a dramatic increase in magnitude with increasing speed. Quantitative analysis shows that while the noise increases by a factor of about 6 the signal actually went up by almost a factor of 10. Thus the signal-to-noise ratio increases for operation at higher speeds, as shown in FIG. 2.

Figure 3:
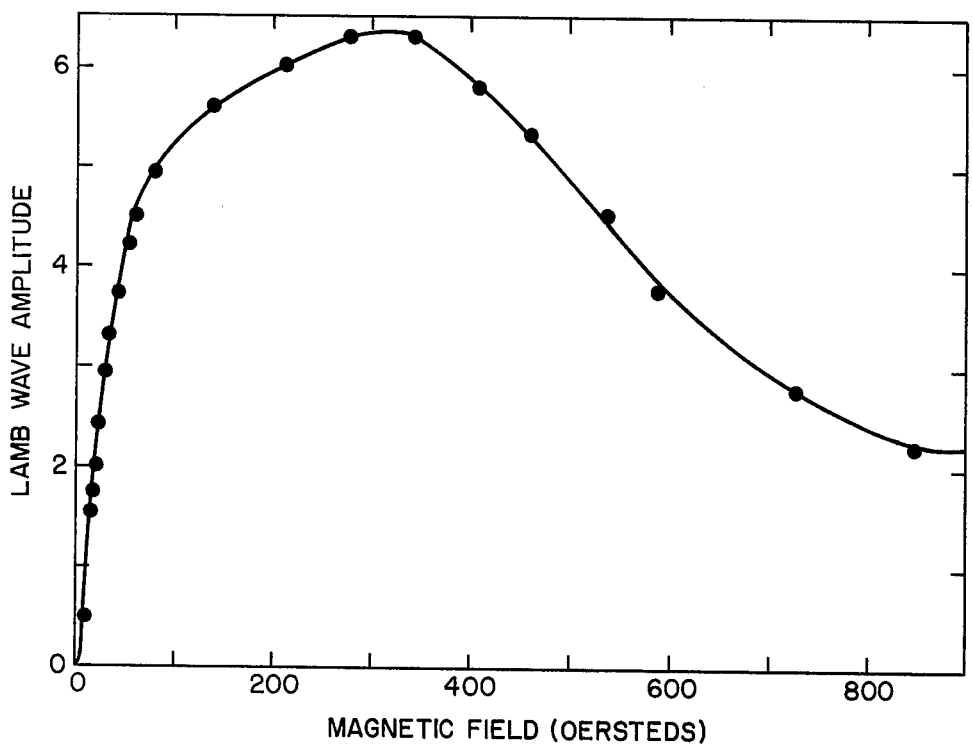
FIG. 3 shows the relation in iron between the amplitude of generated Lamb waves and the density of the magnetic field used to generate the Lamb wave.

In order to determine the origin of this fortuitous and surprising relation between the signal-to-noise ratio and speed, the relation of the magnetic field to the amplitude of the generated Lamb wave and to the speed was measured. FIG. 3 shows how the amplitude of the generated Lamb wave depends upon the intensity of the magnetic field surrounding the coil of the transducer for a ferromagnetic steel such as used in pipelines. The unusual shape of the curve of FIG. 3 arises from a magnetostrictive reaction in the iron under the transducer coil, in addition to the previously described Lorentz reaction. The magnetostrictive component of the wave-creating force depends upon the applied field because the magnetostriction coefficients of iron are field dependent.

FIG. 4 shows the relation of the magnetic field density in the center of the gap to the speed of the iron as it moves past the gap. As shown, the field density is a monatonically increasing function of speed. Thus, the generated signal should follow the curve shown in FIG. 3 as the field density increases and, when considered in conjunction with the previously mentioned noise signal, helps explain the relation between the signal-to-noise ratio and speed.

FIG. 5 shows detailed set of graphs on the distribution of magnetic field along the wall of a 12 inch diameter pipe. Orientation of the magnetic field with respect to the pipe and magnet is shown in FIG. 5b which represents a cross-section of pipe 2 taken along the center of the gap between the poles of magnet 10 as shown in FIG. 1. At zero speed, this field distribution is symmetrical about a line joining the center of the poles of magnet 10. As shown in FIG. 1, such line extends parallel to the length of pipe 2. As the speed increases a strong asymmetry develops which moves the peak field to higher values and closer to the leading edge of the magnet pole pieces. At the same time, the field at the trailing edge of the magnet poles drops dramatically, and actually shows negative values where the pipe emerges from under the pole pieces. Since the pipe is 12 inches in diameter, each 10° equals about 1 inch along the pipe circumference. Thus, at speeds of from 5 to 20 mph, the advantages of the peak field can be obtained by locating the coil 0.5 to 1.6 inches forward of the line joining the center of the poles of the magnet.

These strong field modifications can be explained by induced eddy currents produced when the electrically conducting pipe moves into the magnetic field of the transducer electromagnet. When there is a change in magnetic flux threading a metal there is an induced current, an eddy current, that generates opposite fields so that the flux in the conductor tries to stay fixed. As the flux threading the iron pipe increases when the pipe enters the electromagnet, eddy currents are induced in such a direction as to keep the flux out of the metal and force it to pile up or increase at the surface of the pipe. Conversely, when the pipe wall leaves the magnets, eddy currents flow to hold the flux inside the pipe, thus decreasing the field on the outside near the surface. Since the magnitude of these induced currents is proportional to the rate at which the flux changes, the fields they produce can be expected to be proportional to the speed of the pipe wall. Hence the continual increase in magnetic field with speed shown in the FIGS. 4 and 5.

These eddy current fields are concentrated at the surface of the metal; hence they can be observed by gaussmeter probes held near the surface. Fortunately, the magnetic fields that control the magnitude of Lamb waves that are excited or detected are those that exist just inside the metal surface. Hence, the enhancement of transducer efficiency with increasing speed (as produced by increasing field strength) that is displayed in FIG. 4.

This enhancement of the magnetic fields at the surface by the eddy currents and the fact that the ultrasonic waves are excited by surface stresses constitutes a fundamental advantage of this ultrasonic inspection system over the magnetic flux leakage method that is commonly used today. In the magnetic method, the magnetic flux must penetrate from the I.D. to the O.D. of the pipe before it can sense defects in the O.D. This flux penetration requires a finite time which translates into a finite length dimension for a moving instrument package. Thus, in order for the magnetic flux leakage method to operate in a buried pipe, the inspection station must be long enough to allow the flux to penetrate through the wall before the location of the sensors is reached. In the presented ultrasonic case, the flux need only penetrate to the electromagnetic skin depth of the 130 kHz fields used to excite the Lamb waves (a distance of about 1 mil) and it is the sound waves that interrogate the O.D. of the pipe. Thus the ultrasonic system need be no longer than the 5- or 6-inch length of the Lamb wave transducer.

Figure 6:
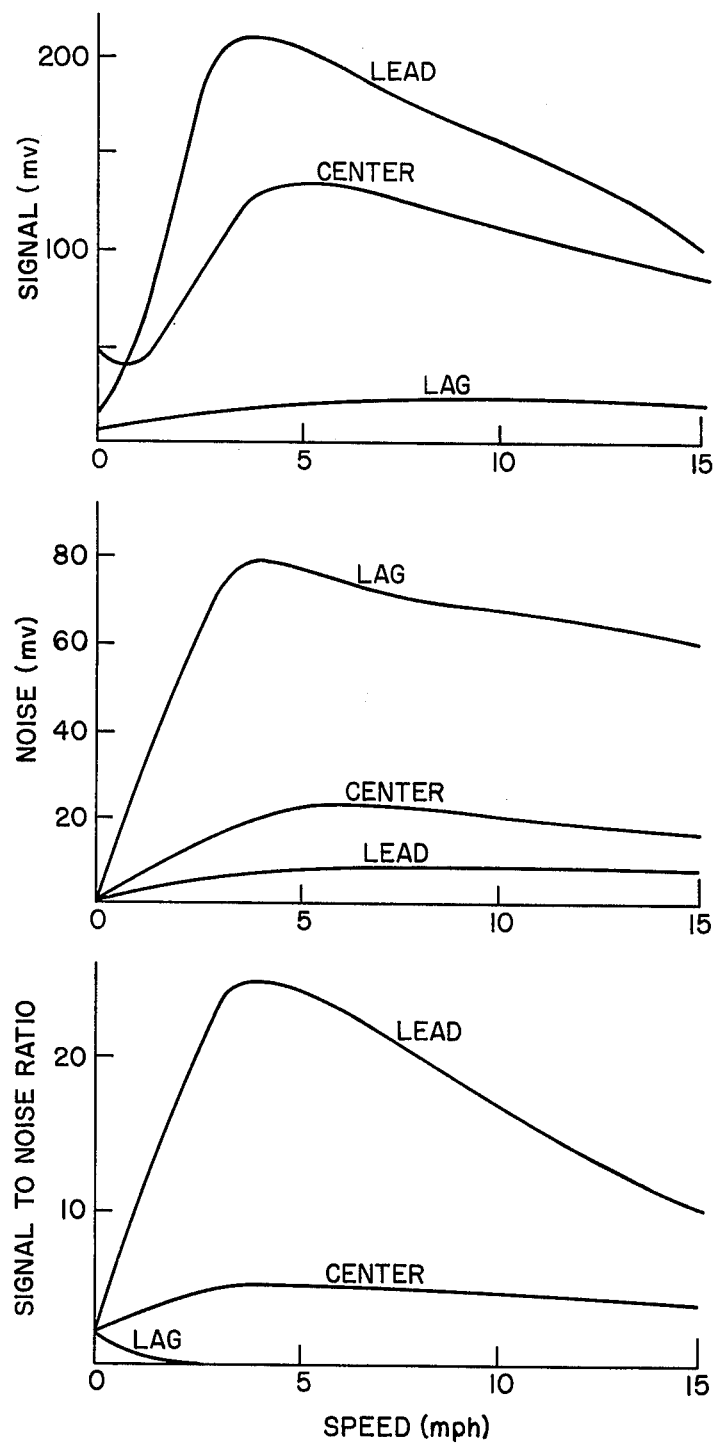
FIG. 6 shows the effect of the coil location and speed on the signal-to-noise ratio.

FIG. 5a shows that as the speed of inspection increases the maximum magnetic field increases and moves away from the center of the magnet pole pieces, toward the region where the pipe is entering the magnet. In addition, the field where the pipe leaves the magnet becomes small and even changes sign. Therefore, the transducer coils should be positioned at the entrance to the magnet where they can take full advantage of the eddy current induced fields. In order to verify this, measurements of the ultrasonic signal and the noise were made as a function of speed with the receiver transducer positioned in three locations. FIG. 6 shows the results. In the lead position, the center of the transducer was aligned with the edge of the magnet poles where the pipe moved into the magnet. In the lag position, the transducer center was next to the edge of the pole pieces where the pipe left the magnet. The figure shows clearly that the ultrasonic signals are maximized and the noise minimized when the transducer lies at the entrance of the magnet.

It can be seen from FIG. 6 that there is a large maximum in efficiency at a speed of about 4 mph for a transducer in the lead position. This maximum corresponds to the maximum in transducer efficiency as a function of magnetic field that was displayed in FIG. 3, wherein the total magnetic field is given by the sum of the applied field and the motion induced eddy current field. At higher speeds, the eddy current field increases and drives the efficiency of the transducer off of the maximum point on the high field side. Therefore, by decreasing the applied field as the speed increases, the total field at the transducer coils can be kept at the value that provides the maximum efficiency.

Figure 7:
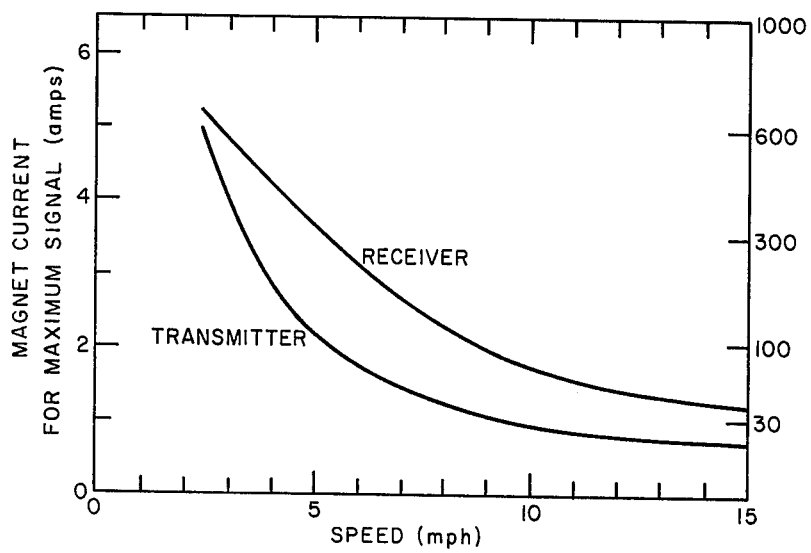
FIG. 7 shows the electromagnet currents required for maximum signal-to-noise ratio as a function of speed.

This effect was demonstrated by operating at a series of fixed speeds and adjusting the current in the transmitter and receiver electromagnets to obtain the maximum received ultrasonic signal strength at each speed. FIG. 7 shows that electromagnet currents required for maximum efficiency decreased as the speed increased, as expected. Using the known value of the electrical resistance of the electromagnet coils, the currents given on the left-hand scale of FIG. 7 can be converted into power requirements and these are shown on the right-hand scale. It can be seen that above about 10 mph, the electromagnet power required by the transmitter and receiver are only approximately 20 and 40 watts respectively. Thus a total of only 60 watts need be drawn from a battery pack as long as the speed remains above 10 mph.

Figure 8:
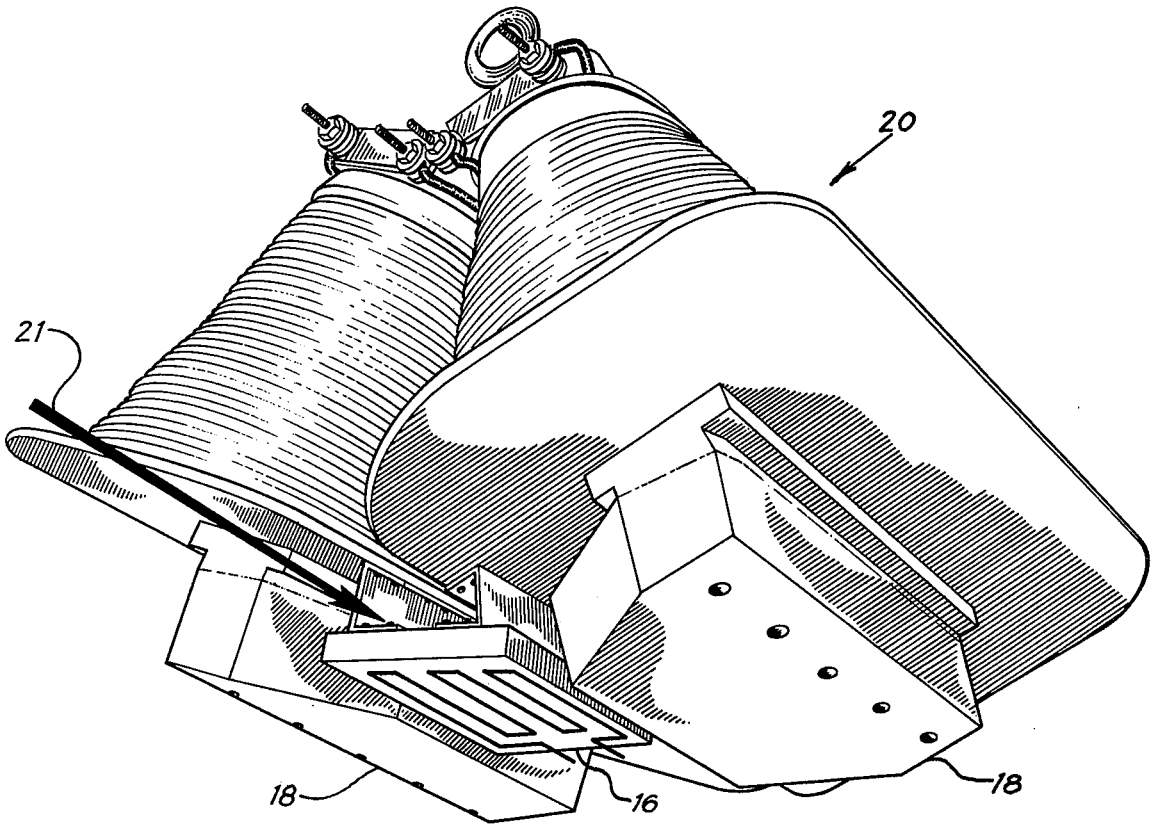
FIG. 8 is transducer for use inside a pipe according to an embodiment of the invention.

FIG. 8 is a transducer constructed according to one embodiment of the invention for use on the previously mentioned inspection station which travels inside pipelines. A meander-type coil 16 is located between the poles 18 of an electromagnet 20. The coil 16 is placed close to, but not in contact with, the inside surface of the pipe. Arrow 21 shows the direction of the oncoming pipe material.

An important feature of the invention is the positioning of the coil 16 predominately on the forward or leading side of the centerline of the poles in order to take advantage of the flux concentration in this area as the station with the magnet moves through the pipeline. The optimum location of the coil can be determined for each speed, depending upon the speed of the station, utilizing curves such as shown in FIG. 5a. Although not shown in FIG. 8, coil 16 can be supported by either the electromagnet or by the frame of the inspection station and its position made adjustable.

The magnetic field can be oriented transversely to the direction of relative motion (as shown in FIG. 1) or parallel to the direction of relative motion, depending upon the direction in which the Lamb wave is to be launched. In either case, the transducer is mounted closer to the leading side of the magnet than to the trailing side in order to obtain a high flux density.

It is clear that the present invention can be used in many applications where it is necessary to efficiently obtain a magnetic field in a part that can be moved relative to the magnets. Electromagnetic transducers can be used to inspect pipe, plate, sheet, and bar as these items move past an inspection station. The invention can be applied to conductive materials that are not ferromagnetic such as aluminum and copper. In some applications, permanent magnets can be used rather than electromagnets such as used to illustrate the invention.

Numerous variation and modifications may be made without departing from the present invention. Accordingly, it should be clearly understood that the form of the present invention described above and shown in the accompanying drawings is illustrative only and is not intended to limit the scope of the present invention.

What is claimed is:

1. An electromagnetic transducer for inducing ultrasonic waves in or receiving the waves from an electrically conductive material for use in inspecting said material as the material moves relative to the transducer, comprising:
   a magnet having magnetic poles for creating a magnetic field transverse to the path of the motion; and
   a coil positioned between the magnetic poles and in the flux path joining the poles of said magnet and centered on the side of said magnet where said magnet and said conductive material are approaching each other.

2. The transducer as claimed in claim 1, wherein said transducer is stationary and the material moves by said transducer.

3. The transducer as claimed in claim 1, wherein the material is held stationary and said transducer moves by the material.

4. The transducer as claimed in claim 1, wherein said magnet comprises an electromagnet.

5. The transducer as claimed in claim 1, wherein said magnet comprises a permanent magnet.

6. An electromagnetic transducer for inducing ultrasonic waves in or receiving the waves from an electrically conductive pipe for use in an inspection station which moves longitudinally inside said pipe, comprising:
   a magnet having circumferentially spaced poles for creating a magnetic field transverse to the direction of movement of the inspection station; and
   a coil having conductors positioned between the spaced poles and transversely to said magnetic field, said coil being located predominantly near the leading side of said magnet where flux is concentrated as said magnet moves through said pipe, whereby maximum transducer efficiency is obtained and the signal-to-noise ratio of the transducer is increased.

7. The transducer as claimed in claim 6, wherein said magnet comprises an electromagnet.

8. A method of increasing the efficiency and of increasing the signal-to-noise ratio of an electromagnet transducer for inducing ultrasonic waves in or receiving the waves from an electrically conductive pipe used for inspecting said pipe comprising:
   providing a magnet having circumferentially spaced poles for positioning a short space from the inside surface of the pipe as said magnet moves through the pipe;
   locating the conductors of a coil between the spaced poles and transverse to the magnetic field created by said magnet and predominately near the leading side of said magnet where flux is concentrated as said magnet moves through said pipe;
   positioning said magnet and coil inside the pipe and spaced from the inside surface of said pipe; and
   moving said magnet and coil through said pipe.

* * * * *